(12) United States Patent
Swennen

(10) Patent No.: US 8,093,034 B2
(45) Date of Patent: Jan. 10, 2012

(54) FED BATCH CULTURE METHODS FOR STREPTOCOCCI

(75) Inventor: Erwin Frans Swennen, Bologna (IT)

(73) Assignee: Novartis AG, Basel (CH)

( * ) Notice: Subject to any disclaimer, the term of this patent is extended or adjusted under 35 U.S.C. 154(b) by 532 days.

(21) Appl. No.: 12/092,209

(22) PCT Filed: Nov. 1, 2006

(86) PCT No.: PCT/IB2006/003938
§ 371 (c)(1),
(2), (4) Date: Aug. 7, 2008

(87) PCT Pub. No.: WO2007/052168
PCT Pub. Date: May 10, 2007

(65) Prior Publication Data
US 2008/0312137 A1 Dec. 18, 2008

(30) Foreign Application Priority Data

Nov. 1, 2005 (GB) .................................. 0522303.7

(51) Int. Cl.
*A61K 38/16* (2006.01)
*C12N 1/20* (2006.01)
*A61P 31/04* (2006.01)
*C12P 19/04* (2006.01)

(52) U.S. Cl. .......................................... 435/243; 435/41
(58) Field of Classification Search ........................ None
See application file for complete search history.

(56) References Cited

U.S. PATENT DOCUMENTS

2005/0208473 A1* 9/2005 Krichevsky et al. .............. 435/4

OTHER PUBLICATIONS

Goncalves V N et al: "Optimization of medium and cultivation conditions for capsular polysaccharide production by *Streptococcus pneumoniae* serotype 23F" Applied Microbiology and Biotechnology, vol. 59, No. 6, Sep. 2002 , pp. 713-717, XP002436899.
Ross R A et al: "Regulation of cell component production by growth rate in the group B *Streptococcus*" Journal of Bacteriology, vol. 181, No. 17, Sep. 1999, pp. 5389-5394.
Paoletti L C et al: "Cell growth rate regulates expression of group b *Streptococcus* type III capsular polysaccharide" Infection and Immunity, vol. 64, No. 4, 1996, pp. 1220-1226.
Merritt J et al: "Development and scale-up of a fed-batch process for the production of capsular polysaccharide from *Haemophilus influenzae*" Journal of Biotechnology, vol. 81, No. 2-3, Aug. 25, 2000, pp. 189-197, XP004210490.
Baruque-Ramos J et al: "Polysaccharide production of *Neisseria meningitidis* (Serogroup C) in batch and fed-batch cultivations" Biochemical Engineering Journal, vol. 23, No. 3, May 1, 2005, pp. 231-240, XP004807392.
He Yi et al: "Increase capsular polysaccharide production using fed-batch." Abstracts of Papers American Chemical Society, vol. 225, No. 1-2, Mar. 23, 2003, p. BIOT 150.
Reinert R R: "Pneumococcal conjugate vaccines—a European perspective" International Journal of Medical Microbiology, vol. 294, No. 5, Oct. 15, 2004, pp. 277-294, XP004960104.
Baker C J et al: "Immune response of healthy women to 2 different group B streptococcal type V capsular polysaccharide-protein conjugate vaccines." The Journal of Infectious Diseases, vol. 189, No. 6, Mar. 15, 2004, pp. 1103-1112, XP002436903.
Lopez R et al: "Recent trends on the molecular biology of pneumococcal capsules, lytic enzymes, and bacteriophage" FEMS Microbiology Reviews, vol. 28, No. 5, Nov. 2004, pp. 553-580, XP004633968.
Goncalves V M et al: "Introduction of air in the anaerobic culture of *Streptococcus pneumoniae* serotype 23F induces the release of capsular polysaccharide from bacterial surface into the cultivation medium" Journal of Applied Microbiology, vol. 101, No. 5, Nov. 2006, pp. 1009-1014, XP002436904.
Wessels M R et al: "Immunogenicity in animals of a polysaccharide-protein conjugate vaccine against type III Group B *Streptococci*" J. Clin. Invest., vol. 86, No. 1990, Nov. 1990, pp. 1428-1433.
Guttormsen H-K et al; "Immunologic memory induced by a glycoconjugate vaccine in a murine adoptive lymphocyte transfer model" Infection and Immunity, vol. 66, No. 5, May 1998, pp. 2026-2032.
Paoletti L C et al: "Synthesis and preclinical evaluation of glycoconjugate vaccines against Group B *Streptococcus* types VI and VIII" The Journal of Infectious Diseases, vol. 180, Aug. 9, 1999, pp. 892-895.
Palazzi D L et al: "Use of type V Group B *Streptococcal* conjugate vaccine in adults 65-85 years old" The Journal of Infectious Diseases, vol. 190, Jun. 30, 2004, pp. 558-564.

* cited by examiner

*Primary Examiner* — Robert A Zeman
(74) *Attorney, Agent, or Firm* — Banner & Witcoff, Ltd.

(57) ABSTRACT

This invention relates to the optimization of culture conditions to improve the production of bacterial capsular polysaccharides from *Streptococcus* strains in fed-batch culture.

15 Claims, 5 Drawing Sheets

FED BATCH CULTURE METHODS FOR STREPTOCOCCI

This application is a national stage application of PCT/IB2006/003938 filed Nov. 1, 2006, which claims the benefit of Serial No. GB 0522303.7 filed Nov. 1, 2005. Each of these applications is incorporated herein by reference in its entirety.

All documents cited herein are incorporated by reference in their entirety.

TECHNICAL FIELD

This invention is in the field of bacterial cultures and specifically relates to the optimisation of culture conditions to improve the production of bacterial capsular polysaccharides.

BACKGROUND ART

Capsular polysaccharides (cps) are important immunogens involved in various bacterial diseases. This feature has lead to them being an important component in the design of vaccines. They have proved useful in eliciting immune responses especially when linked to earner proteins [1]. Typically, capsular polysaccharides are produced using batch culture in complex medium (Group B *Streptococcus, Staphylococcus aureus, Streptococcus pneumoniae* and *Haemophilus influenzae*), fed-batch culture (*H. influenzae*) or continuous culture (Group B *Streptococcus* and *Lactobacillus rhamnosus*) [2-7]. Most studies used batch culture systems in which the growth rate, nutrient levels and metabolic concentrations change during incubation. In such systems, alteration of one factor results in changes in other factors associated with growth. Continuous cultures allow the researcher to separate and define parameters that are interdependent during batch culture growth, such as growth rate, nutrient and product concentrations and cell density. During continuous culture, fresh medium is added to a culture at a fixed rate and cells and medium are removed at a rate that maintains a constant culture volume. Continuous culture was preferred for capsular polysaccharide production when it proved to be dependent on conditions [8].

For Group B *Streptococcus* (GBS, *S. agalactiae*), cell growth rate was reported to be the principal factor regulating capsular polysaccharide production. Furthermore, the production of type III capsular polysaccharide was shown to occur independently of the growth-limiting nutrient. Higher specific yields (up to about 90 mg/gDW) were obtained when cells were held at a fast (0.8, 1.4 or 1.6 h) mass doubling time [$t_d$] rather than at a slow time ($t_d$=2.6 or 11 h) [8-10]. However, continuous culture is prone to strain stability problems and contamination. Furthermore, continuous culture is somewhat expensive due to the continuous feed of medium and nutrients.

There is therefore a need to find alternatives to continuous culture for the high yield production of capsular polysaccharides in order to overcome the problems with continuous culture that are cited above.

DISCLOSURE OF THE INVENTION

We have discovered that high yields of cps can be obtained for any *Streptococcus* strain using fed-batch culture, that is a culture which is initiated by the inoculation of cells into a finite volume of fresh medium and terminated by a single harvest after the cells have grown, with extra nutrients being added to the culture once the initial source of nutrients has been exhausted. Such high yields are comparable to or better than those obtained using continuous culture. Furthermore, the methods disclosed herein are not prone to tire stability and contamination problems of continuous culture.

The invention provides a process for culturing *Streptococcus*, wherein the *Streptococcus* is grown in fed-batch culture. Preferably the *Streptococcus* is GBS. The fed-batch culture may be either fixed volume fed-batch or variable volume fed-batch. In fixed volume fed-batch culture the limiting substrate is fed without diluting the culture (e.g. using a concentrated liquid or gas or by using dialysis). In valuable volume fed-batch culture the volume changes over fermentation time due to the substrate feed. In a method of producing cps from *Streptococcus*, the invention provides the improvement of culturing the *Streptococcus* in fed-batch.

Certain strains of *Streptococcus* are known to be "bad producers" of cps in that typically they produce only low levels of cps in culture. Examples of such bad producers include the GBS strains DK21 and 2603. However, using the methods disclosed herein, high levels of cps can be obtained even from such "bad producers". Therefore the invention provides a process for increasing the cps yield from a strain of *Streptococcus* comprising culturing *Streptococcus* in fed-batch culture wherein, under batch or continuous culture conditions, the strain produces <30 mg cps/g DW (e.g. <10 mg cps/g DW).

Preferably the invention provides a method of culturing *Streptococcus* in fed-batch culture, wherein a high yield of capsular polysaccharide is produced. Preferably the yield of cps is 10 mg/gDW (mg cps per g dry weight of bacteria) or more (e.g. 20, 30, 40, 50, 60, 70, 80, 90, 100, 110, 120, 130, 140, 150, 160, 170, 180, 190, 200 or more), and more preferably >30 mg/g DW. Preferably the yield of cps from the culture medium is 10 mg/L or more (e.g. 20, 30, 40, 50, 60, 70, 80, 90, 100, 120, 140, 160, 180, 200, 220, 240, 260, 280, 300 or more). More preferably, the yield of cps from the culture medium is 50 mg/L or more (e.g. 150, 200, 250, 300, 350, 400, 450, 500, 550, 600, 650 or more). Thus the method of the invention allows the production of cps at a far higher yield per unit volume compared with continuous culture. In some cases, the yield per unit volume may be double or more than double that produced using continuous culture.

An overall culture process may be split into specific phases (batch, fed-batch and carbon-feed) which may be further subdivided. Initially, a batch culture is started during which the culture doubling rate (μ) increases to achieve a low doubling time ($t_d$). The $t_d$ may then increase during a first fed-batch phase (FB1) until gaining the value wanted for production. This doubling rate may then maintained at a steady level during a second fed-batch phase (FB2). Then a carbon feed (GF) is usually started which results in an increase in $t_d$ as non-auxotrophic but limiting ingredients of the medium are progressively depleted. The initial batch phase allows the bacteria to start growing and to achieve a low $t_d$. The fed-batch and carbon feed phases allow the production of CPS at a high rate. The fed-batch phase provides nutrients to the culture as they are used up. The carbon feed phase only provides an additional carbon source, so other nutrients become limiting.

The high yield may be maintained by culturing the bacteria at a low $t_d$ during the fed-batch phase. Preferably this low $t_d$ is maintained through the second fed-batch phase (FB2) in particular. Preferably the $t_d$ is 80 minutes or less, preferably 60 minutes or less (e.g. 58, 56, 54, 52, 50, 49, 48, 47, 46, 45, 44, 43, 42, 41, 40, 38, 36, 34, 32, 30, 25, 20, 15 or less). Preferably the $t_d$ is about 45 minutes (0.75 h) (e.g. 0.6-1.0 h). The $t_d$ may be adjusted by using methods known in the art such as temperature and oxygen concentration or by limiting nutrient levels.

As the skilled person will appreciate, the $t_d$ may be controlled by any one of a number of limiting factors. Generally, the bacteria are allowed to grow freely until a desired $t_d$ has been achieved (the "batch" phase) whereupon a control mechanism is initiated to maintain the $t_d$ (the "fed-batch" phase). Preferably, during the free growth phase the carbon supply is not a limiting factor. However, once the desired $t_d$ has been achieved, any one of a number of limiting factors, including the supply of carbon (although not preferred), may be used to limit growth and to maintain the culture at the desired $t_d$.

In order to maintain the carbon levels during cps production, it is preferred that the carbon source concentration is maintained by using pH-dependent feed. Such a feed may be initiated from the start of the culture or only when a specific $t_d$ has been achieved. However, if the feed is stalled upon initiation of the culture, the feed rate must be maintained higher than the consumption rate to avoid the carbon source from becoming a limiting factor in growth. When the carbon source concentration in the medium decreases, metabolism is reduced and the pH rises. When the pH of the culture rises above a certain threshold pH (pHc), the carbon source is added to the medium. The carbon source feed is stopped when the pH of the culture falls below the pHc value. Preferably the pHc is approximately neutral e.g between 6 and 8 (e.g. 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0). Preferably the pHc is between 6.9 and 7.5. Preferably the pHc is pH7.2.

The invention also provides a method of producing a high yield of cps from *Streptococcus*, wherein the culture includes a phase wherein *Streptococcus* is cultured at a $t_d$ of 45 minutes.

The invention further provides a method for culturing *Streptococcus* comprising initiating a fed-batch culture of *Streptococcus* in medium and monitoring the pH of the culture such that when the pH rises above a threshold value, a carbon source is added to the medium and when the pH drops below the threshold value, the carbon source feed is stopped, whereby the $t_d$ of *Streptococcus* is maintained at 60 minutes or less (e.g. 58, 56, 54, 52, 50, 49, 48, 47, 46, 45, 44, 43, 42, 41, 40, 38, 36, 34, 32, 30, 25, 20, 15 or less). Preferably the $t_d$ is about 45 minutes (0.75 h) (e.g. 0.6-1.2 h). Preferably the threshold pH (pHc) is as defined above, e.g. about pH7.2.

The fermentation can be manually controlled or automated by a computer or other machine. In an embodiment, the pH is monitored on a computer. In a further embodiment, a computer controls and/or adjusts the carbon source feed rate to maintain the pH about a set point (pH is adjusted by the addition of alkali, such as NaOH or $NH_4OH$, or acid, as appropriate). In a further embodiment, a computer controls and/or adjusts the carbon source feed rate to maintain the pH at about a setpoint. In a further embodiment, a computer controls and/or adjusts the oxygen feed rate (and/or agitation, aeration, back pressure, or a combination of these parameters) to maintain the pH at about a setpoint. Other variables may also be monitored and controlled using a computer, such as, but not limited to nitrogen concentration and temperature.

Further embodiments monitor the dissolved oxygen content and/or carbon source concentration with a computer. The use of computer in this application is specifically intended to include all necessary programs, controllers, devices to function as described. The computer may form part of a computer aided device.

Preferably, the invention also provides a control algorithm for controlling the growth of bacteria in a culture wherein the pH of the culture is monitored such that when the pH rises above the pHc, the culture is fed with a carbon source, and when the pH drops below the pHc, feeding stops. Preferably the culture is fed-batch culture. Preferably the bacteria are *Streptococcus*. The algorithm may also control other parameters such as, but not limited to, carbon source concentration, temperature, oxygen saturation and nitrogen concentration.

Following culture, the bacteria may undergo further processing steps to purify the cps and to conjugate it to carrier protein. The invention therefore provides a method comprising a) culturing *Streptococcus* in fed-batch culture and b) purifying cps from the bacteria. The method may further comprise step c) conjugating the capsular saccharide to a carrier protein, to give a protein-saccharide conjugate. The purified cps may undergo further processing steps in order to prepare pharmaceutical preparations. Examples of such steps are given below.

Streptococcus

The *Streptococcus* may be selected from *S. agalactiae* (GBS), *S. pyogenes* (GAS), *S. pneumoniae* (pneumococcus) and *S. mutans*. The *streptococcus* may alternatively be *S. thermophilus* or *S. lactis*. If the *Streptococcus* used is GBS, then preferably the serotype selected is 1a, 1b, 3, 4 or 5. Preferably the strains of GBS used are O90 (1a), 7357 (1b), H36b (1b), DK21 (2), M781 (3) or 2603 (5). If the *Streptococcus* used is *S. pneumoniae*, then preferably the serotypes selected are one or more, or all of 4, 6B, 9V, 14, 18C, 19P, and 23F. Serotype 1 may also preferably be selected. Preferably the serotypes selected are one or more, or all of 1, 3, 4, 5, 6B, 7F, 9V, 14, 18C, 19F, and 23F.

The culture produced using the method of the invention may be homogeneous (i.e. consists of a single species or strain of *Streptococcus*), or may be heterogeneous (i.e. comprises two or more species or strains of *Streptococcus*). Preferably tire culture is homogeneous.

The *Streptococcus* used may be a wild type strain or may be genetically modified. For instance it may be modified to produce non-natural capsular polysaccharides, or heterologous polysaccharides; or to increase yield.

Growth Medium

Any type of liquid growth medium may be used which is suitable for maintaining growth of *Streptococcus* species. Preferred media include complex media such as Columbia broth, LB, Todd-Hewitt, GC medium, blood broth or brain-heart infusion; semi-defined media such as MCDM; chemically defined media for *Streptococcus* such as M1, MC, FMC [11], or C-48 [12]; and media composed for growth of eukaryotic cell lines containing necessary auxotrophic components such as RPMI, spent medium, McCoy's and Eagle's. A typical medium contains yeast extract. By increasing the concentration of the medium, higher ODs may be achieved, resulting in a higher volumetric production of cps. Accordingly, the growth medium will comprise a carbon source, a nitrogen source, a sulphur source and may additionally comprise one or more of an antibiotic and an antifoam agent. Typical antibiotics include kanamycin, ampicillin and tetracycline. The antibiotics may be used to exert a selection pressure to select for particular bacteria which contain an antibiotic resistance gene and/or to select for Gram positive bacteria (e.g. *Streptococci*). This can therefore be used to maintain selection pressure for the bacteria expressing the desired cps. For example, the antibiotic aztrianam is effective against Gram negative, but not Gram positive bacteria. Antifoaming agents are known in the art and may include mineral oil, medical oil, highly formulated polysiloxane glycol copolymers, silicone compounds and emulsions, oxalkylated compounds, mineral oil/synthetic blends, glycol/ester blends, etc.

The culture will also require the addition of various other factors essential for growth, such as, lipids (such as long chain fatty acids such as linoleic or oleic acid), steroids (such as cholesterol), purines and pyrimidines, vitamins and growth factors, amino acids (L- and/or D-form) and/or chemical elements or inorganic ions (such as Fe, K, Mg, Mn, Ca, Co, Cu, P and/or Zn).

If the growth medium contains additives obtained from animals, such as bovine serum albumin, these should be obtained from sources free of transmissible spongiform encephalopathies, to avoid contamination of the medium and eventually the cps.

Carbon Source

The type of carbon source used is not essential. Preferably a primary carbon source is selected from the group consisting of glucose, fructose, lactose, sucrose, maltodextrins, starch, inulin, glycerol, vegetable oils such as soybean oil, hydrocarbons, alcohols such as methanol and ethanol, organic acids such as acetate. More preferably the carbon source is selected from glucose, glycerol, lactose, fructose, sucrose and soybean oil. The term "glucose" includes glucose syrups, i.e. glucose compositions comprising glucose oligomers. The carbon source may be added to the culture as a solid or liquid. Preferably the carbon source is controlled to avoid osmotic stress on the cells which can result in overfeeding. This is usually achieved by not adding all the carbon source required for the duration of the fermentation to the initial batch culture. The carbon source is also controlled to avoid depletion which can result in growth limitation and pigment production [13].

Nitrogen Source

The type of nitrogen source used is not essential. Preferably the nitrogen source is selected from urea, ammonium hydroxide, ammonium salts (such as ammonium sulphate, ammonium phosphate, ammonium chloride and ammonium nitrate), other nitrates, amino acids such as glutamate and lysine, yeast extract, yeast autolysates, yeast nitrogen base, protein hydrolysates (including, but not limited to, peptones, casein hydrolysates such as tryptone and casamino acids), soybean meal, Hy-Soy, tryptic soy broth, cotton seed meal, malt extract, corn steep liquor and molasses. More preferably, a nitrogen source is selected from ammonium hydroxide, ammonium sulphate, ammonium chloride and ammonium phosphate. Most preferably, the nitrogen source is ammonium hydroxide. The use of ammonium hydroxide as a nitrogen source has the advantage that ammonium hydroxide additionally can function as a pH-controlling agent. If ammonium sulphate and/or ammonium phosphate are used as a nitrogen source, at least a portion of the sulphur and/or phosphorus requirement of the microorganism may be met.

Phosphorus Source

As noted above, phosphorus may be added to the growth medium. The phosphorus may be in the form of a salt, in particular it may be added as a phosphate (such as ammonium phosphate as noted above) or polyphosphate. If a polyphosphate is used, it may be in the form of a phosphate glass, such as sodium polyphosphate [14]. Such phosphate glasses are useful as their solubility properties are such that concentrated nutrient medias can be prepared with no resulting precipitation upon mixing.

Other Variables

The temperature of the culture is kept between 30 and 45° C. (e.g. at 31, 32, 33, 34, 35, 36, 37, 38, 39, 40, 41, 42, 43, 44° C.). Preferably the temperature is about 37° C. Thus it may be necessary to heat or cool the vessel containing the culture to ensure a constant culture temperature is maintained. The temperature may be used to control $t_d$, thus for a given culture process, the temperature may be different at different phases (i.e. the batch phase, fed-batch phase and carbon feed phase).

The oxygen feed of the culture may be controlled. Oxygen may be supplied as air, enriched oxygen, pure oxygen or any combination thereof. Methods of monitoring oxygen concentration are known in the art. Oxygen may be delivered at a certain feed rate or may be delivered on demand by measuring the dissolved oxygen content of the culture and feeding accordingly with the intention of maintaining a constant dissolved oxygen content.

The rate of agitation or aeration may also be controlled. This ensures that than nutrients and oxygen are transferred around the bioreactor in which the culture is contained. The relative velocity between the nutrient solution and the individual cell should be around 0.5 m/sec (e.g. 0.1, 0.2, 0.3, 0.4, 0.5, 0.6, 0.7, 0.8, 0.9 or 1.0 m/s).

As noted above, the pH of the culture may be controlled by the addition of acid or alkali. As pH will typically drop during culture, preferably alkali is added. Examples of suitable alkalis include NaOH and $NH_4OH$.

All of these variables may be controlled by the computer, computer aided device or control algorithm as mentioned above.

The alteration of these variables may be used to control the $t_d$ of the culture.

Polysaccharide Preparation

Methods for preparing capsular saccharides from bacteria are well known in the art e.g. see references 15, 16, 17, etc.

For GBS, the following methods may be used (see also ref. 18).

Generally, a small amount of capsular polysaccharide is released into the culture medium during bacterial growth, and so the starting material for alcoholic precipitation of contaminating proteins and/or nucleic acids may thus be the supernatant from a centrifuged bacterial culture. More typically, however, the starting material will be prepared by treating the capsulated bacteria themselves (or material containing the bacterial peptidoglycan), such that the capsular saccharide is released.

Capsular polysaccharide can be released from bacteria by various methods, including chemical, physical or enzymatic treatment. Thus an aqueous preparation of polysaccharide can be treated prior to the initial protein/nucleic acid precipitation reaction.

A typical chemical treatment is base extraction [19] (e.g. using sodium hydroxide), which can cleave the phosphodiester linkage between tire capsular saccharide and the peptidoglycan backbone. As base treatment de-N-acetylates the capsular saccharide, however, later re-N-acetylation may be necessary.

A typical enzymatic treatment involves the use of both mutanolysin and β-N-acetylglucosaminidase [20]. These act on the bacterial peptidoglycan to release the capsular saccharide for use with the invention, but also lead to release of the group-specific carbohydrate antigen. An alternative enzymatic treatment involves treatment with a type II phosphodiesterase (PDE2). PDE2 enzymes can cleave the same phosphates as sodium hydroxide (see above) and can release the capsular saccharide without cleaving the group-specific carbohydrate antigen and without de-N-acetylating the capsular saccharide, thereby simplifying downstream steps. PDE2 enzymes are therefore a preferred option for preparing capsular saccharides.

A preferred starting material for the process of the invention is thus de-N-acetylated capsular polysaccharide, which can be obtained by base extraction as described in reference 19. Another preferred starting material is thus the product of PDE2 treatment of *Streptococcus*. Such materials can be subjected to concentration (e.g. ultrafiltration) prior to precipitation as mentioned below.

Alcoholic Precipitation and Cation Exchange

The *Streptococcus* capsular saccharide obtained after culture will generally be impure and will be contaminated with bacterial nucleic acids and proteins. These contaminants can be removed by sequential overnight treatments with RNase, DNase and protease. As an alternative, rather than remove these contaminants enzymatically, alcoholic precipitation can be used. If necessary (e.g. after base extraction), materials will usually be neutralised prior to the precipitation.

The alcohol used to precipitate contaminating nucleic acids and/or proteins is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol.

The alcohol is preferably added to the polysaccharide suspension to give a final alcohol concentration of between 10% and 50% (e.g. around 30%). The most useful concentrations are those which achieve adequate precipitation of contaminants without also precipitating the polysaccharide. The optimum final alcohol concentration may depend on the bacterial serotype from which the polysaccharide is obtained, and can be determined by routine experiments without undue burden. Precipitation of polysaccharides as ethanol concentrations >50% has been observed.

The alcohol may be added in pure form or may be added in a form diluted with a miscible solvent (e.g. water). Preferred solvent mixtures are ethanol:water mixtures, with a preferred ratio of between around 70:30 and around 95:5 (e.g. 75:25, 80:20, 85:15, 90:10).

The saccharide is also treated with an aqueous metal cation. Monovalent and divalent metal cations are preferred, and divalent cations are particularly preferred, such as $Mg^{++}$, $Mn^{++}$, $Ca^{++}$, etc, as they are more efficient at complex formation. Calcium ions are particularly useful, and so the alcohol mixture preferably includes soluble calcium ions. These may be added to a saccharide/alcohol mixture in the form of calcium salts, either added as a solid or in an aqueous form. The calcium ions are preferably provided by the use of calcium chloride.

The calcium ions are preferably present at a final concentration of between 10 and 500 mM e.g. about 0.1 M. The optimum final $Ca^{++}$ concentration may depend on the *Streptococcus* strain and serotype from which the polysaccharide is obtained, and can be determined by routine experiments without undue burden.

After alcoholic precipitation of contaminating proteins and/or nucleic acids, the capsular polysaccharide is left in solution. The precipitated material can be separated from the polysaccharide by any suitable means, such as by centrifugation. The supernatant can be subjected to microfiltration, and in particular to dead-end filtration (perpendicular filtration) in order to remove particles that may clog filters in later steps (e.g. precipitated particles with a diameter greater than 0.22 µm). As an alternative to dead-end filtration, tangential microfiltration can be used.

Diafiltration

A step of diafiltration may be used after the precipitation of proteins and/or nucleic acids, and before the detergent-mediated precipitation. This diafiltration step is particularly advantageous if base extraction or phosphodiesterase was used for release of the capsular saccharide, as the group-specific saccharide will also have been hydrolysed, to give fragments much smaller than the intact capsular saccharide. These small fragments can be removed by the diafiltration step.

Tangential flow diafiltration is typical. The filtration membrane should thus be one that allows passage of hydrolysis products of the group-specific antigen while retaining the capsular polysaccharide. A cut-off in the range 10 kDa-30 kDa is typical. Smaller cut-off sizes can be used, as the hydrolysis fragments of the group-specific antigen are generally around 1 kDa (5-mer, 8-mer and 11-mer saccharides), but the higher cut-off advantageously allows removal of other contaminants without leading to loss of the capsular saccharide.

At least 5 cycles of tangential flow diafiltration are usually performed e.g. 6, 7, 8, 9, 10, 11 or more.

Cationic Detergent Treatment

Many techniques for precipitating soluble polysaccharides are known in the art. According to the invention, the saccharide is precipitated using one or more cationic detergents. Treating, a mixture of the capsular saccharide and group-specific saccharide with a cationic detergent leads to preferential precipitation of the capsular saccharide, thereby advantageously and conveniently minimising contamination by the group-specific saccharide.

Particularly preferred detergents for use in the process of the invention are tetrabutylammonium and cetyltrimethylammonium salts (e.g. the bromide salts). Cetyltrimethylammonium bromide ('CTAB') is particularly preferred [21]. CTAB is also known as hexadecyltrimethylammonium bromide, cetrimonium bromide, Cetavlon and Centimide. Other detergents include hexadimethrine bromide and myristyltrimethylammonium salts.

The detergent-mediated precipitation step is preferably selective for the capsular polysaccharide. Advantageously, the invention uses a detergent such as CTAB that interacts with sialic acid residues in the saccharide e.g. via carboxyl groups in the sialic acid. The detergent will thus preferentially precipitate the sialic acid-containing capsular saccharides, and particularly longer saccharides within a mixed population, thus minimising contamination by saccharides whose antigenically-important sialic acids may have been damaged in earlier treatment steps.

Re-Solubilisation

After precipitation, the polysaccharide (typically in the form of a complex with the cationic detergent) can be re-solubilised, either in aqueous medium or in alcoholic medium. For aqueous re-solubilisation, the $CTA^-$ cation in the precipitate will generally be replaced by a metal cation; for alcoholic re-solubilisation, the $CTA^-$ cation will generally be retained. The choice of aqueous or alcoholic re-solubilisation may depend on the GBS serotype from which the polysaccharide is obtained, and on any contaminants still present at this stage. For example, pigments are sometimes present in the precipitated pellet, and these can effectively be removed by alcoholic re-solubilisation followed by carbon filtration.

A typical aqueous medium for re-solubilisation will include a metal cation. Monovalent and divalent metal cations are preferred, and divalent cations are particularly preferred, such as $Mg^{++}$, $Mn^{++}$, $Ca^{++}$, etc. Calcium ions are particularly useful, and so re-solubilisation preferably uses $Ca^{++}$, provided by the use of calcium chloride. A $Ca^{++}$ concentration of between 10 and 500 mM (e.g. about 0.1M) is preferred. The optimum final $Ca^{++}$ concentration may depend on the *Strep*-

*tococcus* serotype from which the polysaccharide is obtained, and can be determined by routine experiments without undue burden.

A typical alcoholic medium for re-solubilisation is based on ethanol. The same alcohols used for precipitation of nucleic acids and/or proteins can be used, but the concentration required for precipitation of the capsular saccharide will generally be higher e.g. the alcohol is preferably added to give a final alcohol concentration of between 70% and 95% (e.g. around 70%, 75%, 80%, 85%, 90% or 95%). The optimum final alcohol concentration may depend on the *Streptococcus* serotype from which the polysaccharide is obtained. To achieve the high alcohol concentrations then it is preferred to add alcohol with a low water content e.g. 96% ethanol.

Re-solubilisation will typically occur at room temperature. Acidic conditions are preferably avoided, and re-solubilisation will typically take place at about pH 7.

The re-solubilised material is highly purified relative to the pre-precipitation suspension.

One preferred method for preparing the saccharides involves polysaccharide precipitation followed by solubilisation of the precipitated polysaccharide using a lower alcohol as described above. After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

Another preferred method for preparing the saccharides involves CTAB addition, centrifugation, and collection of supernatant. It may comprise a further round of precipitation with CTAB, centrifugation, and supernatant collection, to provide a paste. The paste may be blended with calcium chloride to give a homogeneous suspension. The suspension can be centrifuged, and the supernatant can be collected e.g. by decanting. Saccharide may be treated by ultrafiltration. Magnesium chloride can then be added, pH can be adjusted to 7.2 to 7.5 (e.g. using sodium hydroxide), and nucleases added. Ethanol can then be added to precipitate nucleic acid and protein. Precipitated material can be removed by centrifugation. Saccharides in the supernatant can be recovered and precipitated by adding ethanol. The saccharide can then be dried, and then dissolved into sodium acetate solution.

The polysaccharide is preferably finally prepared as a dried powder, ready for conjugation.

Conjugate Preparation

After culture of bacteria and preparation of capsular polysaccharides, the saccharides are conjugated to carrier protein(s). In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 22] and is a well known technique [e.g. reviewed in refs. 23 to 31].

Preferred carrier proteins are bacterial toxins or toxoids, such as diphtheria toxoid or tetanus toxoid. The CRM197 mutant of diphtheria toxin [32-34] is a particularly preferred carrier for, as is a diphtheria toxoid. Other suitable carrier proteins include the *N. meningitidis* outer membrane protein [35], synthetic peptides [36,37], heat shock proteins [38,39], pertussis proteins [40,41], cytokines [42], lymphokines [42], hormones [42], growth factors [42], artificial proteins comprising multiple human CD4+ T cell epitopes from various pathogen-derived antigens [43] such as N19 [44], protein D from *H. influenzae* [45,46], pneumococcal surface protein PspA [47], pneumolysin [48], iron-uptake proteins [49], toxin A or B from *C. difficile* [50], a GBS protein (see below) [51], etc.

Attachment to the carrier is preferably via a —NH$_2$ group e.g. in the side chain of a lysine residue in a carrier protein, or of an arginine residue. Where a saccharide has a free aldehyde group then this can react with an amine in the carrier to form a conjugate by reductive amination. Such a conjugate may be created using reductive amination involving an oxidised galactose in the saccharide (from which an aldehyde is formed) and an amine in the carrier or in the linker. Attachment may also be via a —SH group e.g. in the side chain of a cysteine residue.

It is possible to use more than one carrier protein e.g. to reduce the risk of carrier suppression. Thus different carrier proteins can be used for different *Streptococcus* strains or serotypes e.g. GBS serotype Ia saccharides might be conjugated to CRM197 while serotype Ib saccharides might be conjugated to tetanus toxoid. It is also possible to use more than one earner protein for a particular saccharide antigen e.g. serotype III saccharides might be in two groups, with some conjugated to CRM197 and others conjugated to tetanus toxoid. In general, however, it is preferred to use the same carrier protein for all saccharides.

A single carrier protein might carry more than one saccharide antigen [52,53]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide protein ratio (w/w) of between excess protein (e.g. 1:5) and excess saccharide (e.g. 5:1) are preferred. Ratios between 1:2 and 5:1 are preferred, as are ratios between 1:1.25 and 1:2.5. Ratios between 1:1 and 4:1 are also preferred. With longer saccharide chains, a weight excess of saccharide is typical. In general, the invention provides a conjugate, wherein the conjugate comprises a *Streptococcus*, preferably a *S. agalactiae* capsular saccharide moiety joined to a carrier, wherein the weight ratio of saccharide:carrier is at least 2:1.

Compositions may include a small amount of free carrier. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [54, 55, etc.]). Other suitable techniques use carbodiimides, hydrazides, active esters, norborane, p-nitrobenzoic acid, N-hydroxysuccinimide, S-NHS, EDC, TSTU; see also the introduction to reference 29).

Linkages via a linker group may be made using any known procedure, for example, the procedures described in references 56 and 57. One type of linkage involves reductive animation of the polysaccharide, coupling the resulting amino group with one end of an adipic acid linker group, and then coupling a protein to the other end of the adipic acid linker group [27, 58, 59]. Other linkers include B-propionamido [60], nitrophenyl-ethylamine [61], haloacyl halides [62], glycosidic linkages [63], 6-aminocaproic acid [64], ADH [65], $C_4$ to $C_{12}$ moieties [66], etc. As an alternative to using a linker, direct linkage can be used. Direct linkages to the protein may comprise oxidation of the polysaccharide followed by reductive animation with the protein, as described in, for example, references 67 and 68.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with earner protein is preferred. Another preferred reaction uses CDAP activation with a protein D carrier.

After conjugation, free and conjugated saccharides can be separated. There are many suitable methods, including hydrophobic chromatography, tangential ultrafiltration, diafiltration, etc. (see also refs. 69 & 70, etc.).

Where the composition of the invention includes a depolymerised oligosaccharide, it is preferred that depolymerisation precedes conjugation e.g. is before activation of the saccharide.

In one preferred conjugation method, a saccharide is reacted with adipic acid dihydrazide. For serogroup A, carbodiimide may also be added at this stage. After a reaction period, sodium cyanoborohydride is added. Derivatised saccharide can then be prepared e.g. by ultrafiltration. The derivatized saccharide is then mixed with carrier protein (e.g. with a diphtheria toxoid), and carbodiimide is added. After a reaction period, the conjugate can be recovered.

Other Steps

As well as including the steps described above, methods of the invention may include further steps. For example, the methods may include a step of depolymerisation of the capsular saccharides, after they are prepared from the bacteria but before conjugation. Depolymerisation reduces the chain length of the saccharides and may not be good for GBS. For *Streptococcus*, especially GBS, longer saccharides tend to be more immunogenic than shorter ones [71].

After conjugation, the level of unconjugated carrier protein may be measured. One way of making this measurement involves capillary electrophoresis [72] (e.g. in free solution), or micellar electrokinetic chromatography [73].

After conjugation, the level of unconjugated saccharide may be measured. One way of making this measurement involves HPAEC-PAD [69].

After conjugation, a step of separating conjugated saccharide from unconjugated saccharide may be used. One way of separating these saccharides is to use a method that selectively precipitates one component. Selective precipitation of conjugated saccharide is preferred, to leave unconjugated saccharide in solution, e.g. by a deoxycholate treatment [69].

After conjugation, a step of measuring the molecular size and/or molar mass of a conjugate may be carried out. In particular, distributions may be measured. One way of making these measurements involves size exclusion chromatography with detection by multiangle light scattering photometry and differential refractometry (SEC-MALS/RI) [74].

Conjugate Combinations

Individual conjugates can be prepared as described above, for any *Pneumococcus* serogroup. Preferably conjugates are prepared for one or more of serogroups 1, 3, 4, 5, 6B, 7F, 9V, 14, 18C, 19F, and 23F. The individual conjugates can then be mixed, in order to provide a polyvalent mixture.

It is also possible to mix a selected number of conjugates to provide a bivalent, trivalent, tetravalent, 5-valent, 6-valent, 7-valent or 11-valent mixture (e.g. to mix 1+3+4+5+6B+7F+9V+14+18C+19F+23F, 4+6B+9V+14+18C+19F+23F or 1+4+6B+9V+14+18C+19F+23F, etc).

For GBS, conjugates are preferably prepared from one or more of serogroups Ia, Ib or III.

Conjugates may be mixed by adding them individually to a buffered solution. A preferred solution is phosphate buffered physiological saline (final concentration 10 mM sodium phosphate). A preferred concentration of each conjugate (measured as saccharide) in the final mixture is between 1 and 20 µg/ml e.g. between 5 and 15 µg/ml, such as around 8 µg/ml. An optional aluminum salt adjuvant may be added at this stage (e.g. to give a final $Al^{3+}$ concentration of between 0.4 and 0.5 mg/ml).

After mixing, the mixed conjugates can be sterile filtered.

Pharmaceutical Compositions

Conjugates prepared by methods of the invention can be combined with pharmaceutically acceptable carriers. Such carriers include any carrier that does not itself induce the production of antibodies harmful to the individual receiving the composition. Suitable earners are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 75.

Compositions may include an antimicrobial, particularly if packaged in a multiple dose format.

Compositions may comprise detergent e.g. a Tween (polysorbate), such as Tween 80. Detergents are generally present at low levels e.g. <0.01%.

Compositions may include sodium salts (e.g. sodium chloride) to give tonicity. A concentration of 10±2 mg/ml NaCl is typical.

Compositions will generally include a buffer. A phosphate buffer is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Conjugates may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 76], or mixtures of different mineral compounds, with the compounds taking any suitable form (e.g. gel, crystalline, amorphous, etc.), and with adsorption being preferred. The mineral containing compositions may also be formulated as a particle of metal salt [77].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 76; see also ref. 78] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 76]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, tire saponin is QS21. A method of production of QS21 is disclosed in ref. 79. Saponin formulations may also comprise a sterol, such as cholesterol [80].

Combinations of saponins and cholesterols can be used to form unique particles called immunostimulating complexes (ISCOMs) [chapter 23 of ref. 76]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 80-82. Optionally, the ISCOMS may be devoid of additional detergent [83].

A review of the development of saponin based adjuvants can be found in refs. 84 & 85.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 86-91. Virosomes are discussed further in, for example, ref: 92

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 93. Such "small particles" of 3dMPL are small enough to be sterile filtered through a 0.22 μm membrane [93]. Other non-toxic LPS derivatives include monophosphoryl lipid A mimics, such as aminoalkyl glucosaminide phosphate derivatives e.g. RC-529 [94,95].

Lipid A derivatives include derivatives of lipid A from *Escherichia coli* such as OM-174. OM-174 is described for example in refs. 96 & 97.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 98, 99 and 100 disclose possible analog substitutions e.g. replacement of guanosine with 2'-deoxy-7-deazaguanosine. The adjuvant effect of CpG oligonucleotides is further discussed in refs. 101-106.

The CpG sequence may be directed to TLR9, such as the motif GTCGTT or TTCGTT [107]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 108-110. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 107 & 111-113.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 114 and as parenteral adjuvants in ref. 115. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 116-123. Numerical reference for amino acid substitutions is preferably based on the alignments of the A and B subunits of ADP-ribosylating toxins set forth in ref. 124, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [125], etc.) [126], interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [127] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [128].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 76)

Examples of liposome formulations suitable for use as adjuvants are described in refs. 129-131.

J. Polyoxy Ethylene Ether and Polyoxyethylene Ester Formulations

Adjuvants suitable for use in the invention include polyoxyethylene ethers and polyoxyethylene esters [132]. Such formulations further include polyoxyethylene sorbitan ester surfactants in combination with an octoxynol [133] as well as polyoxyethylene alkyl ethers or ester surfactants in combination with at least one additional non-ionic surfactant such as an octoxynol [134]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 135 and 136.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 137 and 138.

The invention may also comprise combinations of aspects of one or more of the adjuvants identified above. For example, the following adjuvant compositions may be used in the invention: (1) a saponin and an oil-in-water emulsion [139]; (2) a saponin (e.g. QS21)+a non-toxic LPS derivative (e.g. 3dMPL) [140]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [141]; (5) combinations of 3dMPL with, for example, QS21 and/or oil-in-water emulsions [142]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 76.

The use of an aluminium hydroxide and/or aluminium phosphate adjuvant is particularly preferred, and antigens are generally adsorbed to these salts. Calcium phosphate is another preferred adjuvant.

The composition may be sterile and/or pyrogen-free. Compositions may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, tire taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each streptococcal conjugate is between 1 μg and 20 μg per conjugate (measured as saccharide).

Thus the invention provides a method for preparing a pharmaceutical composition, comprising the steps of: (a) preparing a conjugate as described above; (b) mixing the conjugate with one or more pharmaceutically acceptable carriers.

The invention further provides a method for preparing a pharmaceutical product, comprising the steps of: (a) preparing a conjugate as described above; (b) mixing the conjugate with one or more pharmaceutically acceptable carriers; and (c) packaging the conjugate/carrier mixture into a container, such as a vial or a syringe, to give a pharmaceutical product. Insertion into a syringe may be performed in a factory or in a surgery.

The invention also provides a method for preparing a pharmaceutical composition from a saccharide-protein conjugate, comprising the step of admixing the conjugate with a pharmaceutically acceptable carrier, wherein the conjugate has been prepared by a process conjugation method as described above. The conjugation method and the admixing step can be performed at very different times by different people in different places (e.g. in different countries).

The invention also provides a method for packaging a saccharide-protein conjugate into a pharmaceutical product, wherein the conjugate has been prepared by a process conjugation method as described above. The conjugation method and the packaging step can be performed at very different times by different people in different places (e.g. in different countries).

Pharmaceutical Uses

The invention also provides a method of treating a patient, comprising administering the composition to the patient. The patient may either be at risk from the disease themselves or may be a pregnant woman ('maternal immunisation'). The patient is preferably a human. The human can be of any age e.g. <2 years old, from 2-11 years old, from 11-55 years old, >55 years old, etc.

The invention also provides the composition for use in therapy. The invention also provides the use of the composition in the manufacture of a medicament for the treatment of disease. Preferably the disease is influenza or pneumonia.

Compositions will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration (e.g. to the thigh or the upper arm) is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 143 & 144]. Injectable compositions are preferred.

Further Antigenic Components of Compositions of the Invention

The methods of the invention may also comprise tire steps of mixing a streptococcal conjugate with one or more of the following further antigens:

a saccharide antigen from *Haemophilus influenzae* B [e.g. chapter 14 of ref. 145].

a purified protein antigen from serogroup B of *Neisseria meningitidis*.

an outer membrane preparation from serogroup B of *Neisseria meningitidis*.

an antigen from hepatitis A virus, such as inactivated virus [e.g., 146, 147].

an antigen from hepatitis B virus, such as the surface and/or core antigens [e.g. 147, 148].

a diphtheria antigen, such as a diphtheria toxoid [e.g. chapter 13 of ref. 145]

a tetanus antigen, such as a tetanus toxoid [e.g. chapter 27 of ref. 145].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 149 & 150; chapter 21 of ref. 145].

polio antigen(s) [e.g. 151, 152] such as IPV [chapter 24 of ref. 145].

measles, mumps and/or rubella antigens [e.g. chapters 19, 20 & 26 of ref. 145].

influenza antigen(s) [e.g. chapter 17 of ref. 145], such as the haemagglutinin and/or neuraminidase surface proteins.

an antigen from *Moraxella catarrhalis* [e.g. 153].

a protein antigen from *Streptococcus agalactiae* (group B streptococcus) [e.g. 154, 155].

an antigen from *Streptococcus pyogenes* (group A streptococcus) [e.g. 155, 156, 157].

an antigen from *Staphylococcus aureus* [e.g. 158].

The composition may comprise one or more of these further antigens.

Toxic protein antigens may be detoxified where necessary (e.g. detoxification of pertussis toxin by chemical and/or genetic means [150]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Antigens in the composition will typically be present at a concentration of at least 1 µg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Preferred non-streptococcal antigens for inclusion in compositions are those which protect against *Haemophilus influenzae* type B (Hib). Typically this will be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented. The invention may use any suitable Hib conjugate. Suitable carrier proteins are described above, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to CRM$_{197}$ via an adipic acid linker [159, 160]. Tetanus toxoid is also a preferred carrier.

Administration of the Hib antigen preferably results in an anti-PRP antibody concentration of ≧0.15 μg/ml, and more preferably ≧1 μg/ml.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [161] or it may be non-adsorbed [162]. Prevention of adsorption can be achieved by selecting the correct pH during antigen/adjuvant mixing, an adjuvant with an appropriate point of zero charge, and an appropriate order of mixing for the various different antigens in a composition [163].

Compositions of the invention may comprise more than one Hib antigen. Hib antigens may be lyophilised e.g. for reconstitution by meningococcal compositions. Thus a Hib antigen may be packaged separately from meningococcal conjugates, or may be admixed with them.

Other non-streptococcal antigens for including in compositions of the invention are those derived from a sexually transmitted disease (STD). Such antigens may provide for prophylaxis or therapy for STDs such as chlamydia, genital herpes, hepatitis (such as HCV), genital warts, gonorrhoea, syphilis and/or chancroid [164]. Antigens may be derived from one or more viral or bacterial STDs. Viral STD antigens for use in the invention may be derived from, for example, HIV, herpes simplex virus (HSV-1 and HSV-2), human papillomavirus (HPV), and/or hepatitis (HCV). Bacterial STD antigens for use in the invention may be derived from, for example, *Neisseria gonorrhoeae, Chlamydia trachomatis, Treponema pallidum, Haemophilus ducreyi* or *E. coli*.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Establishment of Optimal Growth-Rate for High Specific Yield

To determine the best growth rate for specific capsular polysaccharide production, many continuous cultures were run at different dilutions. Capsular polysaccharide content was determined using the chemical dosing method to quantify sialic acid [165]. As the method was applied to a complex sample, interferences were determined using a non-encapsulated mutant strain (COH1-13) [166]. The method was validated by spiking with sialic acid and purified capsular polysaccharide. The results were also cross-validated by chromatography.

Figure 1A:
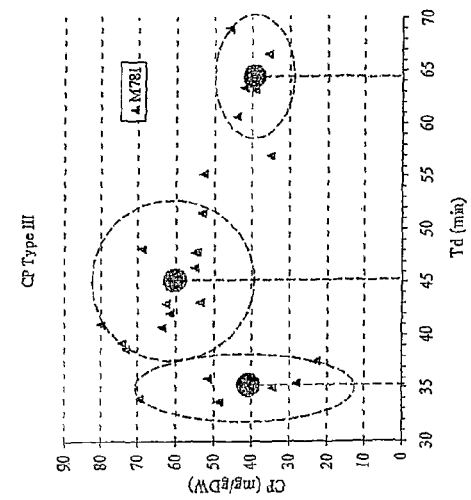
FIG. 1 shows the specific production of (A) Type 1a capsular polysaccharide, (B) Type 1b capsular polysaccharide and (C) Type 3 capsular polysaccharide during different continuous fermentations and at different growth-rates. The specific capsular polysaccharide values are expressed in mg/gDW.
Figure 1B:
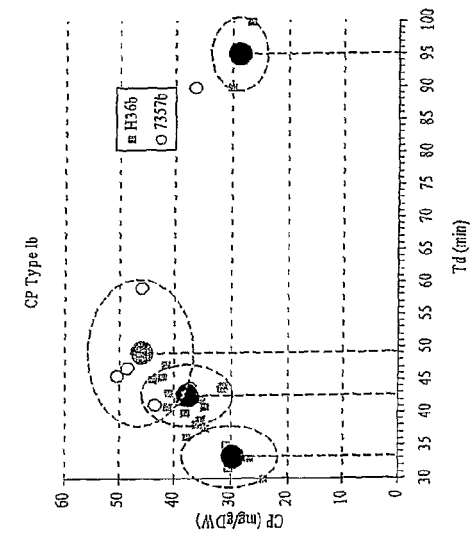
Figure 1C:
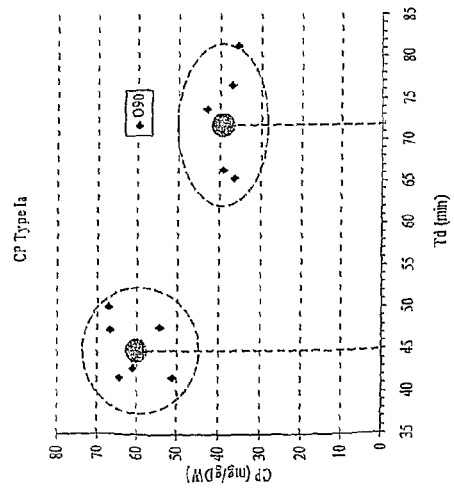

Type 1a strain O90 was shown to produce 1.5 times more capsular polysaccharide at a fast growth rate than a slow one (see FIG. 1A). Type 1b strain H36b was tested at an even faster growth rate than that used for strain O90 (a $t_d$ of <35 mins). However, this very fast growth rate produced a lower yield than that produced at a $t_d$ of 45 mins. As for all strains tested, increasing the $t_d$ to 95 mins caused a further reduction in capsular polysaccharide yield. Strain 7357b showed the same pattern with relation to the culture doubling time, but was able to produce 70% more capsular polysaccharide of serotype Ib than strain H36b (see FIG. 1B). Serotype 3 capsular polysaccharide was produced using strain M781 (FIG. 1C). Again, optimal production of capsular polysaccharide occurred at a $t_d$ of 45 mins, while faster (35 mins) and slower (64 mins) growth rates resulted in lower capsular polysaccharide yield. Table 1 summarises the results of the experiments. The mean yield of capsular polysaccharide for a $t_d$ of 45 mins (0.75 h) proved to be statistically different from that achieved at a $t_d$<0.6 h or $t_d$>1 h (using the unpaired student t-test). Optimum yield occurred at 0.6 h<$t_d$<1 h.

TABLE 1

| Strain/type | $T_d$ (h) | Yield cps (mg/g dry weight) | Student t-test |
| --- | --- | --- | --- |
| O90-1a | 0.76 ± 0.07 | 60.6 ± 2.8 | <0.001 |
|  | 1.21 ± 0.11 | 38.2 ± 3.0 |  |
| H36b-1b | 0.56 ± 0.04 | 29.6 ± 4.2 | <0.001 |
|  | 0.70 ± 0.05 | 37.5 ± 3.9 |  |
|  | 1.58 ± 0.12 | 28.3 ± 2.3 | <0.01 |
| 7357b-1b | 0.79 ± 0.11 | 44.9 ± 5.1 |  |
| M781-3 | 0.56 ± 0.07 | 39.2 ± 16.9 | <0.001 |
|  | 0.75 ± 0.08 | 62.1 ± 9.3 |  |
|  | 1.11 ± 0.16 | 40.3 ± 4.1 | <0.001 |

Figure 2:
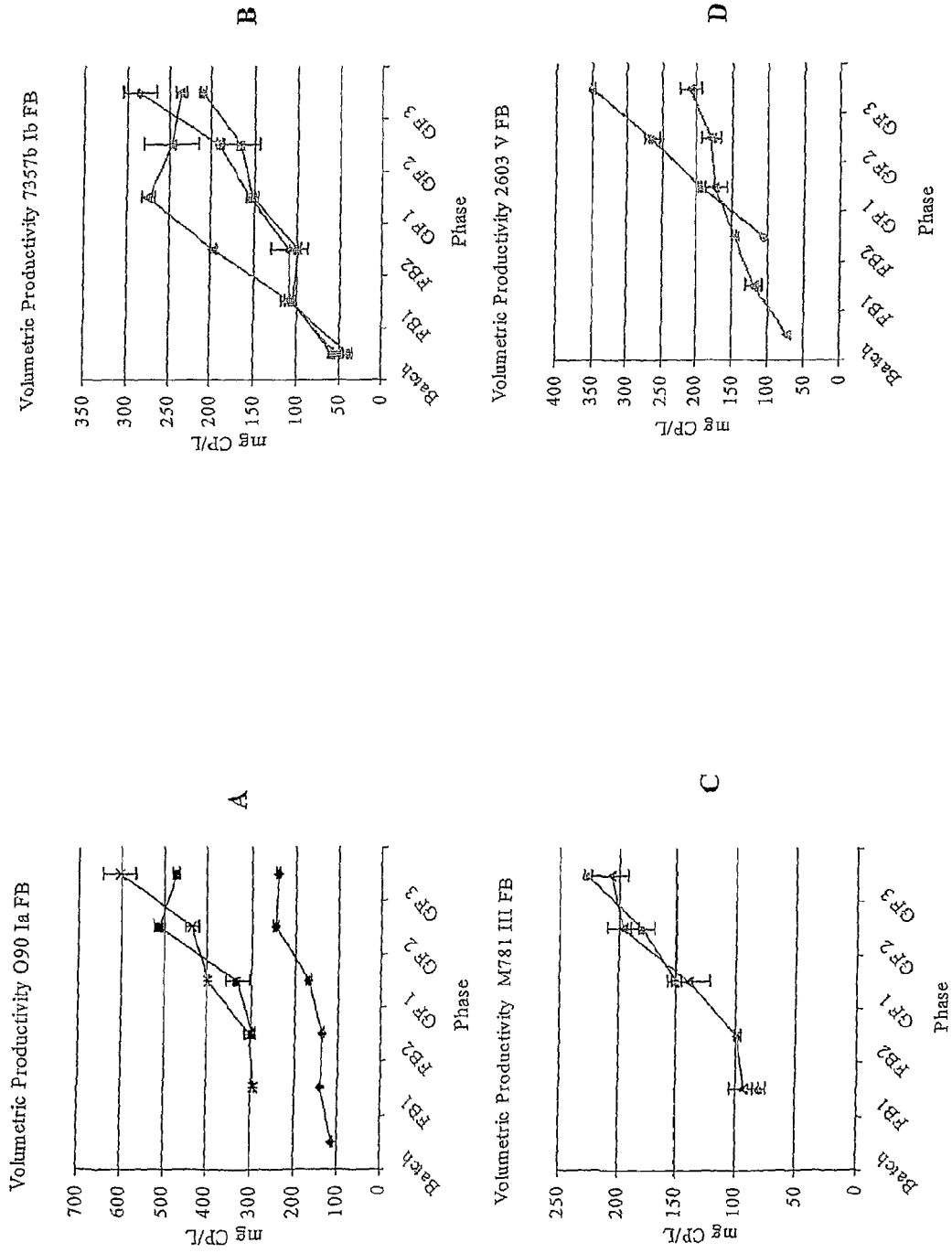
FIG. 2 shows how volumetric productivity increases throughout fed-batch culture.

Volumetric productivity increased during the various phases of fed-batch culture (batch, fed-batch [FB] and carbon feed [GF]) for all four strains of *Streptococcus* tested (FIG. 2). During complex medium feed, the increase is due to the increment of specific product. Increase during the carbon feed (which in this case is glucose) is due to higher biomass production.

Figure 3:
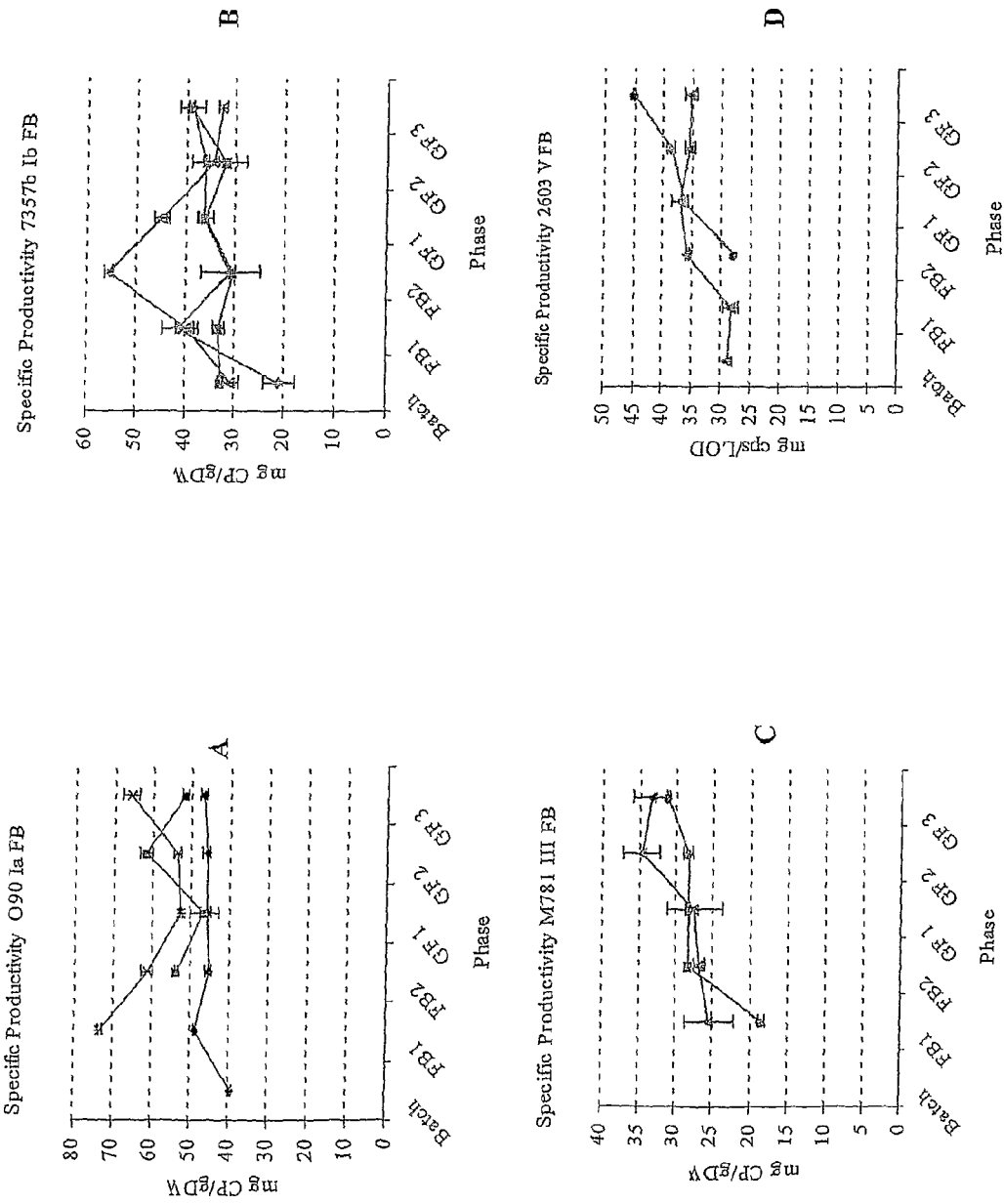
FIG. 3 shows how specific productivity does not decrease throughout fed-batch culture.

Similarly, specific productivity was also shown to increase from batch phase to the end of the fed-batch (FB2) phase (FIG. 3). Then for strains O90 and 7357b (FIGS. 3a & b) the productivity remained constant from FB2 until the end of the pH-regulated carbon feed phase (GF3). However, the productivity of strains M781 and 2603 (FIGS. 3c & d) continued to increase from FB2 to GF3.

Fed-Batch Culture with Exponential Feed

Fed-Batch with Final pH-Controlled Glucose Feed

Figure 4:
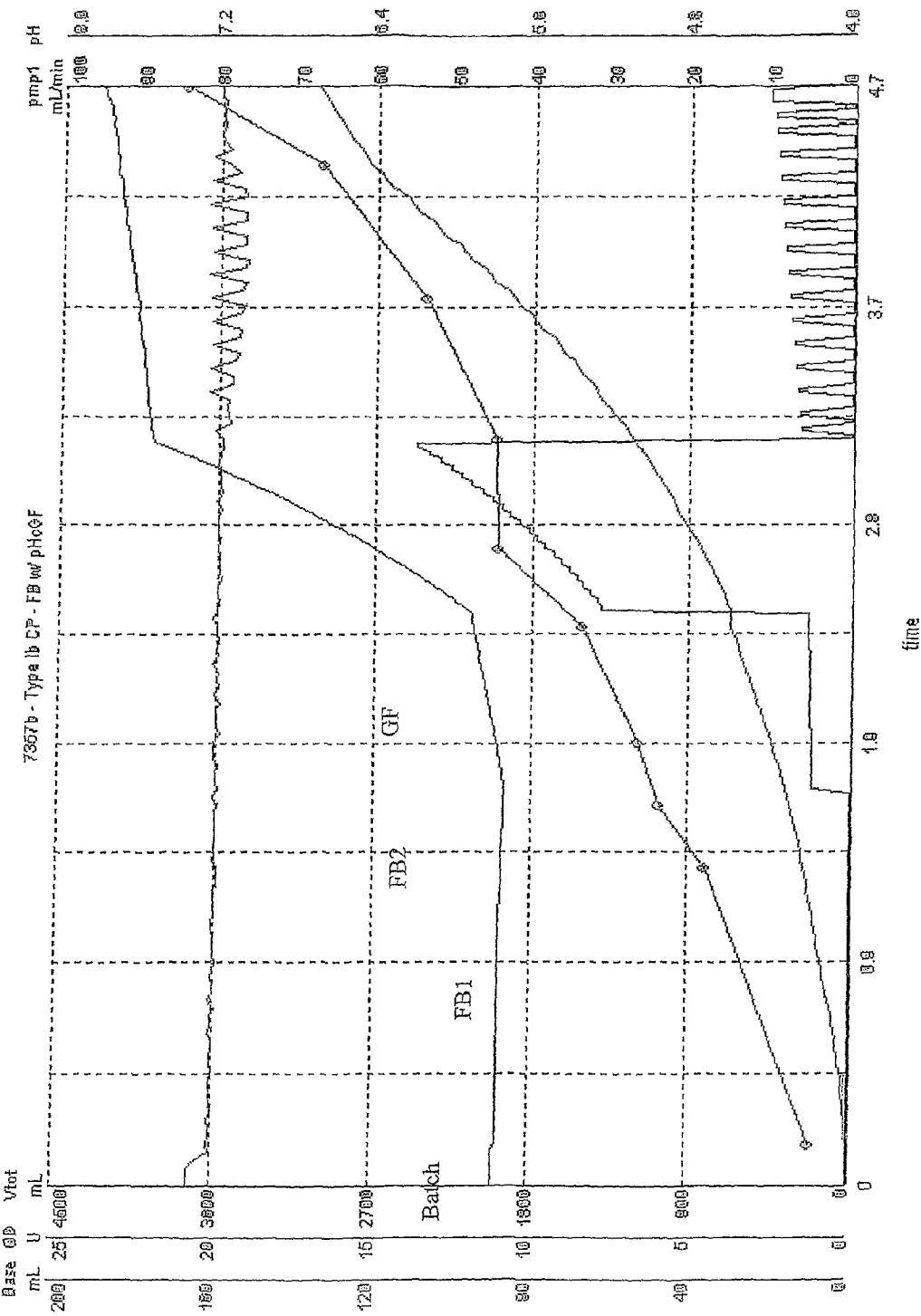
FIG. 4 shows a complex medium fed-batch culture with final pH-regulated glucose starvation control.

The culture was growth in batch to OD>5.5, at which time an exponential feed of complex medium started with a dilution rate (D) of 0.138 h$^{-1}$ (FB1). When the culture reached OD>7.5, the dilution rate was increased to 1.08 h$^{-1}$ (FB2). A steady state with a $t_d$ of 45 min was maintained until a final volume of 5 L was reached. At this time, a pH controlled carbon feed (GF) was activated (which in this case was a glucose feed) with the pHc set at pH7.2, and growth continued up to OD=16, with a progressive decrease of growth rate (see FIG. 4).

Analysis of cps content at various time points showed that specific cps production was maintained at the same level as was seen for the continuous culture, but at a much higher culture density.

pH Control of Glucose Feed

As group B *streptococcus* produces a lot of acid metabolites, even under optimal aerobic conditions (as it lacks a part of the Krebs cycle), the culture pH drops under the pHc (the base pump is activated only gradually) when the strain is allowed to grow without limitations (i.e. in presence of glucose). When glucose concentration falls under a certain level, the metabolic rate of the organism is reduced and the pH rises to 7.2 (set-point of regulation–pHc value).

Figure 5:
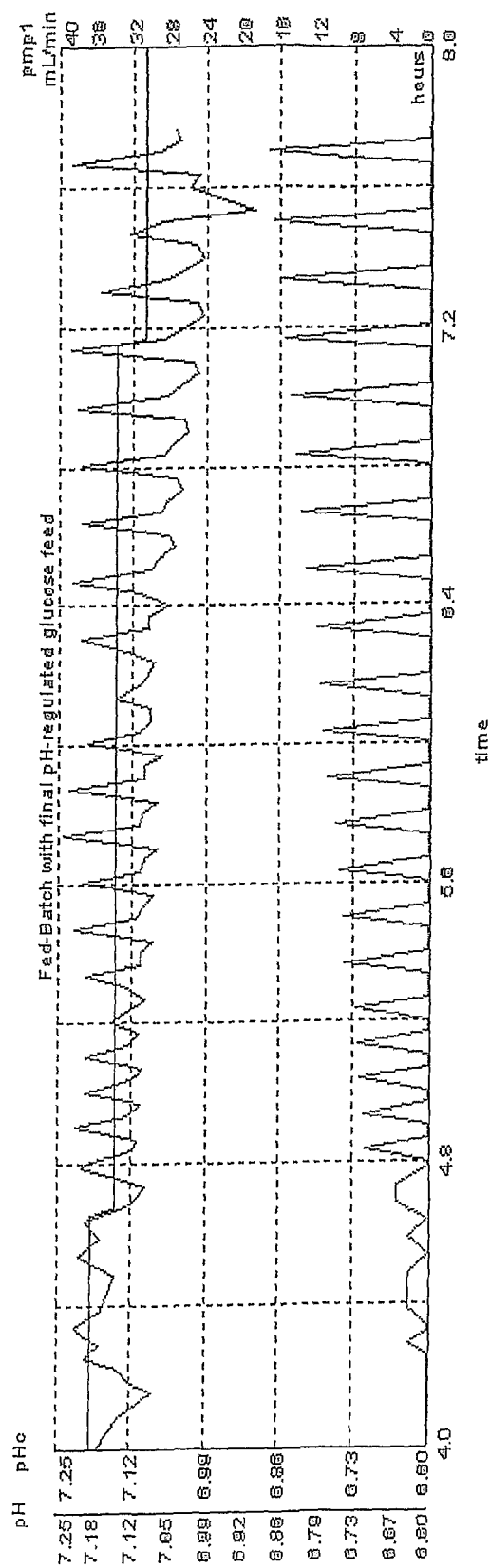
FIG. 5 shows the pH control of the glucose feed.

A control algorithm was programmed to start glucose feeding when pH reaches the pHc value and stop it when pH goes beneath (see FIG. 5). In this case, the glucose feed was only started once the final culture volume of 5 L had been reached.

Confronting Volumetric Productivity

Fed-batch fermentation of O90 offers a method to double the volumetric productivity (P), as pH controlled glucose feeding allows a high OD.

Strains DK21 and 2603 obtained ODs up to 21 (9.45 gDW/L). Both are known to be bad capsular polysaccharide producers, but fed-batch with controlled glucose-feed offers an acceptable solution to obtain their capsular polysaccharides. Thus high yields of capsular polysaccharide can be produced using fed-batch culture, thus avoiding the problems associated with continuous culture. A comparison of the different strains tested and the respective yields can be seen in Table 2. For certain strains, up to double the volumetric productivity can be achieved using fed-batch culture.

TABLE 2

| Type/Strain/Culture (continuous - CC, or fed-batch-FB) | OD at production | P (mgcps/L) | Cps (mg/g dry weight) |
| --- | --- | --- | --- |
| 1a/O90/CC | 8.4 | 248 ± 12 | 60.6 ± 2.8 |
| 1a/O90/FB + pHcGF | 16.0 | 539 ± 94 | 58.8 ± 9.8 |
| 1b/H36b/CC | 9.3 | 95 ± 10 | 37.5 ± 3.9 |
| 1b/H36/FB + pHcGF | 12.7 | 194 | 15.2 |
| 1b/7357/CC | 9.5 | 148 ± 19 | 44.9 ± 5.1 |
| 1b/7357/FB + pHcGF | 21.1 | 245 ± 38 | 36.9 ± 3.5 |
| 3/M781/CC | 9.6 | 228 ± 34 | 62.1 ± 9.3 |
| 3/M781/FB + pHcGF | 16.6 | 217 ± 11 | 32.3 ± 1.6 |
| 2/DK21/FB + pHcGF | 21.1 | 204 ± 17 | 29.7 ± 2.5 |
| 5/2603/FB + pHcGF | 16.4 | 278 ± 100 | 44.4 ± 0.8 |

Experiments were also carried out using a 5× concentrated complex medium containing 150 g/L yeast extract under fed batch conditions (the "standard" medium contained only 16.66 g/L yeast extract). The results of the fermentations are shown in Table 3.

TABLE 3

| Type/Strain/Culture | OD at production | P (mgcps/L) | Cps (mg/g dry weight) |
| --- | --- | --- | --- |
| 1a/O90 | 16.3 | 847 | 51.9 |
| 1a/O90 | 17.6 | 865 | 49.1 |
| 1a/O90 | 17.4 | 835 | 48.0 |
| 1b/H36b | 12.1 | 133 | 11.0 |
| 1b/H36b | 16.8 | 180 | 10.7 |
| 3/M781 | 15.7 | 461 | 29.4 |
| 3/M781 | 18.4 | 309 | 16.8 |
| 5/CJB111 | 29.0 | 159 | 5.5 |
| 5/CJB111 | 25.1 | 411 | 16.4 |

These results show that the use of a concentrated medium allows growth at a higher OD, resulting in a generally higher volumetric production of cps, but a lower specific production (mg/g dry weight). The results also showed that CJB11 could be grown to a higher OD than 2603V, making it more useful for commercial production of serotype V cps.

It will be understood that the invention has been described by way of example only and modifications may be made whilst remaining within the scope and spirit of the invention.

REFERENCES

The Contents of which are Hereby Incorporated in Full

[1] Ada & Isaacs (2003) *Clin Microbiol Infect* 9:79-85
[2] Shen et al. (2001) *Vaccine* 19:850-61
[3] Palazzi et al. (2004) *J. Infect. Dis.* 190:558-64
[4] Merritt et al. (2000) *J. Biotech.* 81:189-97
[5] Dassy & Fournier (1996) *Infect. Immun.* 64:2408-14
[6] Suarez el al (2001) *Appl. Env. Microbiol.* 67:969-71
[7] Wicken et al. (1983) *J. Bact.* 153:84-92
[8] Paoletti et al. (1996) *Infect. Immunol.* 64:1220-1226
[9] Ross et al. (1999) *J. Bact.* 181:5389-5394
[10] Paoletti et al. (1999) *J. Infect. Dis.* 180:892-895
[11] Terleckyj et al. (1975) *Infect. Immunol.* 11:649-55
[12] Willett & Morse (1966) *J. Bacteriol.* 91(6):2245-50
[13] Merritt et al. (1978) *J. Clin. Microbiol.* 8:105-7
[14] WO95/29986
[15] WO98/32873.
[16] Frash (1990) p. 123-145 of *Advances in Biotechnological Processes* vol. 13 (eds. Mizrahi & Van Wezel)
[17] European patent 0072513.
[18] UK patent application 0502096.1
[19] U.S. Pat. No. 6,248,570.
[20] Deng et al. (2000) *J Biol Chem* 275:7497-7504.
[21] Inzana (1987) *Infect. Immun.* 55:1573-79.
[22] Ramsay et al. (2001) *Lancet* 357(9251):195-196.
[23] Lindberg (1999) *Vaccine* 17 Suppl 2:S28-36.
[24] Buttery & Moxon (2000) *J R Coll Physicians Lond* 34:163-168.
[25] Ahmad & Chapnick (1999) *Infect Dis Clin North Am* 13:113-33, vii.
[26] Goldblatt (1998) *J. Med. Microbiol.* 47:563-567.
[27] European patent 0477508.
[28] U.S. Pat. No. 5,306,492.
[29] WO98/42721.
[30] Dick et al. in *Conjugate Vaccines* (eds. Cruse et al.) Karger, Basel, 1989, 10:48-114.
[31] Hermanson *Bioconjugate Techniques*, Academic Press, San Diego (1996) ISBN: 0123423368.
[32] Anonymous (January 2002) *Research Disclosure*, 453077.
[33] Anderson (1983) *Infect Immun* 39(1):233-238.
[34] Anderson et al. (1985) *J Clin Invest* 76(1):52-59.
[35] EP-A-0372501.

[36] EP-A-0378881.
[37] EP-A-0427347.
[38] WO93/17712
[39] WO94/03208.
[40] WO98/58668.
[41] EP-A-0471177.
[42] WO91/01146
[43] Falugi et al. (2001) *Eur J Immunol* 31:3816-24.
[44] Baraldo et al. (2004) *Infect Immun* 72:4884-87.
[45] EP-A-0594610.
[46] WO00/56360.
[47] WO02/091998.
[48] Kuo et al. (1995) *Infect Immun* 63:2706-13.
[49] WO01/72337
[50] WO00/61761.
[51] WO2004/041157
[52] WO99/42130.
[53] WO2004/011027.
[54] Lees et al. (1996) *Vaccine* 14:190-198.
[55] WO95/08348.
[56] U.S. Pat. No. 4,882,317
[57] U.S. Pat. No. 4,695,624
[58] Porro et al. (1985) *Mol Immunol* 22:907-919.
[59] EP-A-0208375
[60] WO00/10599
[61] Gever et al. Med. Microbiol. Immunol, 165: 171-288 (1979).
[62] U.S. Pat. No. 4,057,685.
[63] U.S. Pat. Nos. 4,673,574; 4,761,283; 4,808,700.
[64] U.S. Pat. No. 4,459,286.
[65] U.S. Pat. No. 4,965,338
[66] U.S. Pat. No. 4,663,160.
[67] U.S. Pat. No. 4,761,283
[68] U.S. Pat. No. 4,356,170
[69] Lei et al. (2000) *Dev Biol* (Basel) 103:259-264.
[70] WO00/38711; U.S. Pat. No. 6,146,902.
[71] Wessels et al. (1998) *Infect Immun* 66:2186-92.
[72] Lamb et al. (2000) *Dev Biol* (Basel) 103:251-258.
[73] Lamb et al. (2000) *Journal of Chromatography A* 894: 311-318.
[74] D'Ambra et al. (2000) *Dev Biol* (Basel) 103:241-242.
[75] Gennaro (2000) *Remington: The Science and Practice of Pharmacy*. 20th edition, ISBN: 0683306472.
[76] *Vaccine Design* . . . (1995) eds. Powell & Newman. ISBN: 030644867X. Plenum.
[77] WO00/23105.
[78] WO90/14837.
[79] U.S. Pat. No. 5,057,540.
[80] WO96/33739.
[81] EP-A-0109942.
[82] WO96/11711.
[83] WO00/07621.
[84] Barr et al. (1998) *Advanced Drug Delivery Reviews* 32:247-271.
[85] Sjolanderet et al. (1998) *Advanced Drug Delivery Reviews* 32:321-338.
[86] Niikura et al. (2002) *Virology* 293:273-280.
[87] Lenz et al. (2001) *J Immunol* 166:5346-5355.
[88] Pinto et al. (2003) *J Infect Dis* 188:327-338.
[89] Gerber et al. (2001) *Virol* 75:4752-4760.
[90] WO03/024480
[91] WO03/024481
[92] Gluck et al. (2002) *Vaccine* 20:B10-B16.
[93] EP-A-0689454.
[94] Johnson et al. (1999) *Bioorg Med Chem Lett* 9:2273-2278.
[95] Evans et al. (2003) *Expert Rev Vaccines* 2:219-229.
[96] Meraldi et al. (2003) *Vaccine* 21:2485-2491.
[97] Pajak et al. (2003) *Vaccine* 21:836-842.
[98] Kandimalla et al. (2003) *Nucleic Acids Research* 31:2393-2400.
[99] WO02/26757.
[100] WO99/62923.
[101] Krieg (2003) *Nature Medicine* 9:831-835.
[102] McCluskie et al. (2002) *FEMS Immunology and Medical Microbiology* 32:179-185.
[103] WO98/40100.
[104] U.S. Pat. No. 6,207,646.
[105] U.S. Pat. No. 6,239,116.
[106] U.S. Pat. No. 6,429,199.
[107] Kandimalla et al. (2003) *Biochemical Society Transactions* 31 (part 3):654-658.
[108] Blackwell et al. (2003) *J Immunol* 170:4061-4068.
[109] Krieg (2002) *Trends Immunol* 23:64-65.
[110] WO01/95935.
[111] Kandimalla et al. (2003) *BBRC* 306:948-953.
[112] Bhagat et al. (2003) *BBRC* 300:853-861.
[113] WO03/035836.
[114] WO95/17211.
[115] WO98/42375.
[116] Beignon et al. (2002) *Infect Immun* 70:3012-3019.
[117] Pizza et al. (2001) *Vaccine* 19:2534-2541.
[118] Pizza et al. (2000) *Int J Med Microbiol* 290:455-461.
[119] Scharton-Kersten et al. (2000) *Infect Immun* 68:5306-5313.
[120] Ryan et al. (1999) *Infect Immun* 67:6270-6280.
[121] Partidos et al. (1999) *Immunol Lett* 67:209-216.
[122] Peppoloni et al. (2003) *Expert Rev Vaccines* 2:285-293.
[123] Pine et al. (2002) *J Control Release* 85:263-270.
[124] Domenighini et al. (1995) *Mol Microbiol* 15:1165-1167.
[125] WO99/40936.
[126] WO99/44636.
[127] Singh et al] (2001) *J Cont Release* 70:267-276.
[128] WO99/27960.
[129] U.S. Pat. No. 6,090,406
[130] U.S. Pat. No. 5,916,588
[131] EP-A-0626169.
[132] WO99/52549.
[133] WO01/21207.
[134] WO01/21152.
[135] Andrianov et al. (1998) *Biomaterials* 19:109-115.
[136] Payne et al. (1998) *Adv Drug Delivery Review* 31:185-196.
[137] Stanley (2002) *Clin Exp Dermatol* 27:571-577.
[138] Jones (2003) *Curr Opin Investig Drugs* 4:214-218.
[139] WO99/11241.
[140] WO94/00153.
[141] WO98/57659.
[142] European patent applications 0835318, 0735898 and 0761231.
[143] Almeida & Alpar (1996) *J. Drug Targeting* 3:455-467.
[144] Agarwal & Mishra (1999) *Indian J Exp Biol* 37:6-16.
[145] *Vaccines* (2004) eds. Plotkin & Orenstein. ISBN 0-7216-9688-0.
[146] Bell (2000) *Pediatr Infect Dis J* 19:1187-1188.
[147] Iwarson (1995) *APMIS* 103:321-326.
[148] Gerlich et al. (1990) *Vaccine* 8 Suppl:S63-68 & 79-80.
[149] Gustafsson et al. (1996) *N. Engl. J. Med.* 334:349-355.
[150] Rappuoli et al. (1991) *TIBTECH* 9:232-238.
[151] Sutter et al. (2000) *Pediatr Clin North Am* 47:287-308.
[152] Zimmerman & Spann (1999) *Am Fam Physician* 59:113-118, 125-126.
[153] McMichael (2000) *Vaccine* 19 Suppl 1:S101-107.

[154] Schuchat (1999) *Lancet* 353(9146):51-6.
[155] WO02/34771.
[156] Dale (1999) *Infect Dis Clin North Am* 13:227-43, viii.
[157] Ferretti et al. (2001) *PNAS USA* 98: 4658-4663.
[158] Kuroda et al. (2001) *Lancet* 357(9264): 1225-1240; see also pages 1218-1219.
[159] Kanra et al. (1999) *The Turkish Journal of Paediatrics* 42:421-427.
[160] Ravenscroft et al. (2000) *Dev Biol* (Basel) 103: 35-47.
[161] WO97/00697.
[162] WO02/00249.
[163] WO96/37222; U.S. Pat. No. 6,333,036.
[164] WO00/15255.
[165] Svennerholm (1957) *Biochem. Biophys. ACTA* 24:604-11
[166] Rubens et al. (1987) *Proc Natl Acad Sci* 84:7208-12

The invention claimed is:

1. A process for culturing *Streptococcus*, wherein the *Streptococcus* is grown in fed-batch culture comprising:
   a batch phase;
   a fed-batch phase in which nutrients are provided to the culture and in which a limiting nutrient level is used to limit growth and to maintain the culture at a desired doubling time; and
   a carbon-feed phase in which an additional carbon source is provided so that nutrients other than carbon become limiting.

2. A process according to claim 1 wherein during the fed-batch phase mass doubling time ($t_d$) is maintained at 80 minutes or less.

3. A process according to claim 2 wherein the $t_d$ is maintained at 45 minutes.

4. A process according to claim 1 wherein the carbon level is maintained using a pH-dependent feed.

5. A process according to claim 4, wherein the pH-dependent feed is controlled by a set-pH point (pHc) wherein when the pH of the culture rises above the pHc the carbon source is added to the medium and when the pH of the culture falls below the pHc, the carbon feed is stopped.

6. A process according to claim 5 wherein the pHc is between 6 and 8.

7. A process according to claim 6 wherein the pHc is 7.2.

8. A process according to claim 4 wherein the pH-dependent feed is a pH-dependent glucose feed.

9. A process according to claim 1 wherein the *Streptococcus* is Group B *Streptococcus*.

10. A process according to claim 9 wherein the Group B *Streptococcus* is a strain selected from the group consisting of O90, 7357, H36b, DK21, M781, and 2603.

11. A process according to claim 1 wherein the culture has an oxygen feed.

12. A process according to claim 1 wherein the bacteria are cultured at a $t_d$ of 0.6-1.0 h during the fed-batch phase.

13. A process according to claim 1 wherein the fed-batch phase comprises feeding with a complex medium.

14. A process according to claim 1 wherein the fed batch phase is further subdivided into a first fed-batch phase in which the culture doubling time is increased to a desired value and a second fed-batch phase in which the doubling time is maintained at a steady level.

15. A method for culturing *Streptococcus* comprising initiating a fed-batch culture of *Streptococcus* in medium and monitoring the pH of the culture such that when the pH rises above a threshold value, a carbon source is added to the medium and when the pH drops below the threshold value, the carbon source feed is stopped, whereby the $t_d$ of *Streptococcus* is maintained at 80 minutes or less.

* * * * *